US00PP10989P

United States Patent [19]

Flemer, III

[11] Patent Number: Plant 10,989

[45] Date of Patent: Jun. 29, 1999

[54] *PRUNUS SARGENTII* PLANT NAMED 'PRINCETON SNOWCLOUD'

[75] Inventor: William Flemer, III, Plainsboro Township, Middlesex County, N.J.

[73] Assignee: Treesearch, Allentown, N.J.

[21] Appl. No.: 08/916,387

[22] Filed: Aug. 22, 1997

[51] Int. Cl.[6] ..... A01H 5/00

[52] U.S. Cl. ..... Plt./182

[58] Field of Search ..... Plt./37, 182

*Primary Examiner*—Howard J. Locker
*Assistant Examiner*—Melissa L. Kimball
*Attorney, Agent, or Firm*—James A. Lucas

[57] ABSTRACT

A new and distinct Prunus plant characterized by having a very vigorous growth, being one third larger than sibling seedlings in the same row, and for its very abundant, large white flowers, unusual in the species which normally bears pink flowers. The autumn foliage turns a brilliant red color in late October. It is the most cold hardy of the white Japanese cherry trees.

2 Drawing Sheets

BACKGROUND OF THE INVENTION

This invention relates to Prunus and primarily to a Prunus hybrid which is a product of crossing a seed parent *Prunus sargentii* 'Columnaris', an unpatented cultivar, with an unknown pollen parent.

I first discovered this plant in a row of *Prunus sargentii* seedlings in a nursery near Plainsboro Township, N.J. I asexually reproduced the plant by grafting on bare root understocks in a cultivated area of the nursery. I have observed the plants thus produced and find that the characteristics initially observed are in fact reproduced in successive generations.

Prunus includes a varied and diversified group of ornamental woody plants. Most of these plants are grown for their fruit in addition to their ornamental value. The Prunus species that do no produce edible cherries are predominately grown for ornamental purposes. *Prunus sargentii* is one such species. Originating in Japan, it is the hardiest of the oriental cherry trees. The flowers are a deep pink. It is a wide-spreading tree with brilliant scarlet autumn foliage which addes to its ornamental attractiveness. *Prunus sargentii* 'Columnaris' has all the qualities of *P. sargentii* but is columnar in habit, although the tree will grow wider as it grows older.

BRIEF SUMMARY OF THE INVENTION

The plant of this application is characterized by having a very vigorous growth, being one third larger than sibling seedlings in the same row, and for its very abundant, large white flowers, unusual in the species which normally bears pink flowers. The autumn foliage turns a brilliant red color in late October. It is the most cold hardy of the white Japanese cherry trees known to be as observed in USDA hardiness zone 5-A.

DESCRIPTION OF THE DRAWINGS

This new variety of Prunus is illustrated by the accompanying photographic drawings and depicts the plant by the best possible color representation using color photography.

BOTANICAL DESCRIPTION OF THE PLANT

Figure 1:
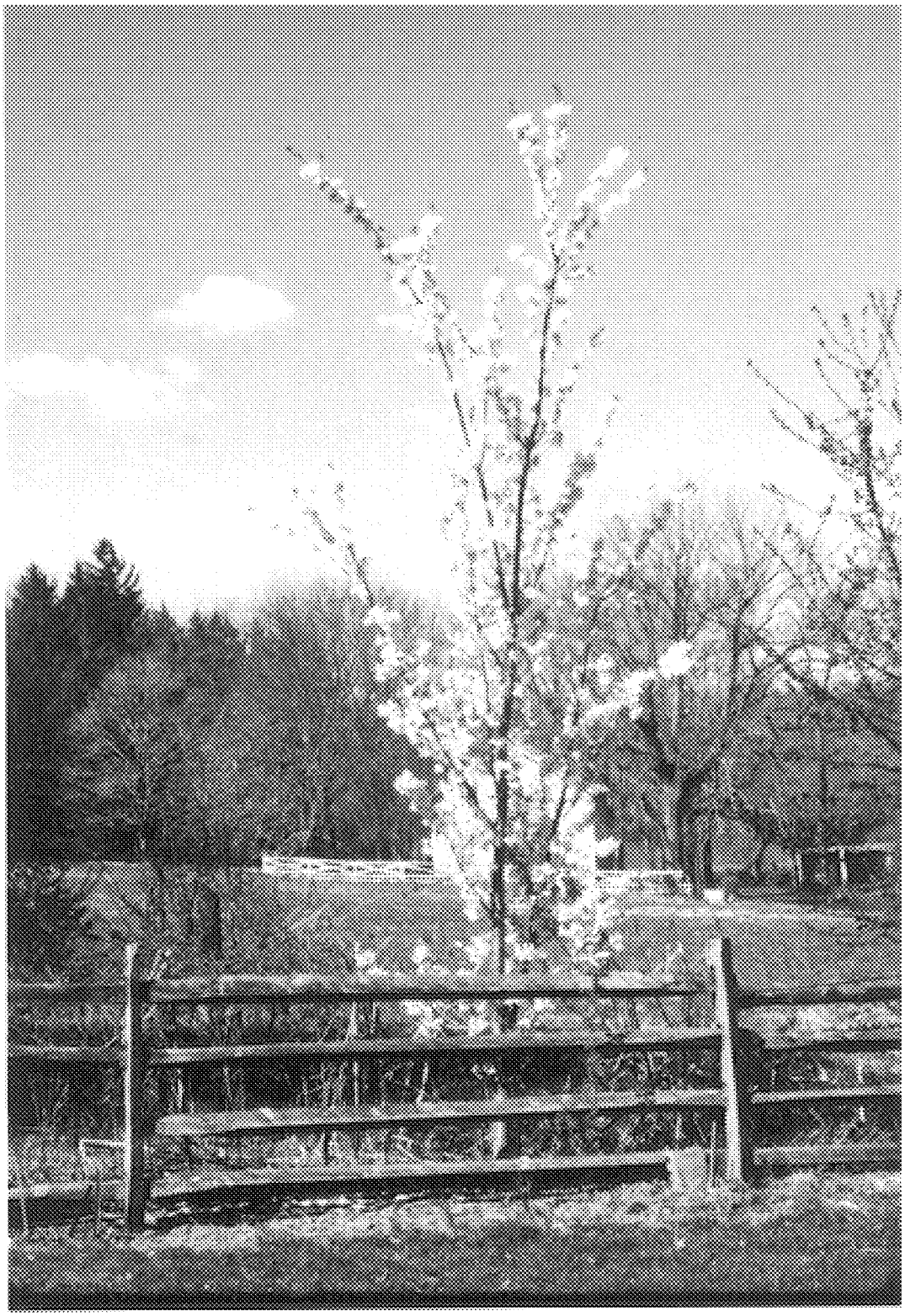
FIG. 1 is a view showing the entire tree.
Figure 2:
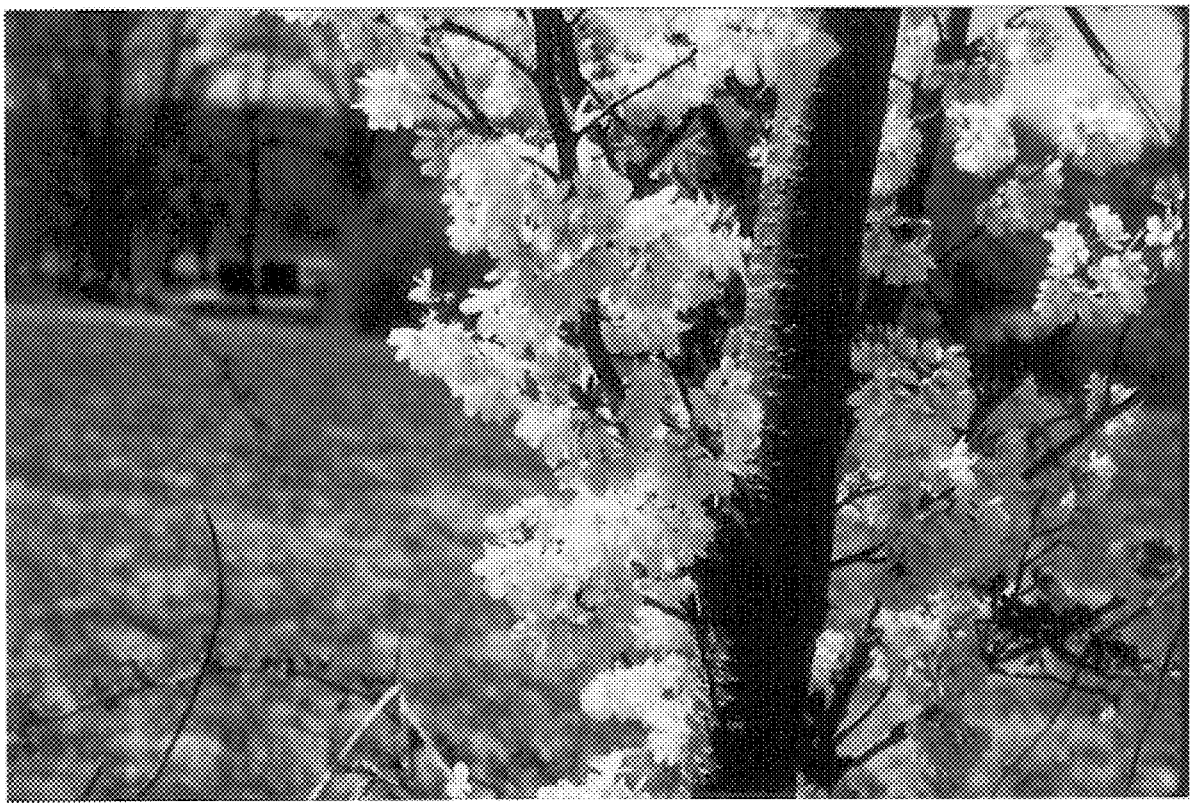
FIG. 2 is a view showing a close-up of the flowers.

The details were observed at a nursery in Plainsboro Twp., N.J. in 1983.

All color references below are measured against the Munsell Color Chart. Colors are approximate as color depends on horticultural practices such as light level and fertilization rate, among others.

Parentage:
- *Seed parent.*—*Prunus sargentii* 'Columnaris'.
- *Pollen parent.*—Unknown.
- *Newly found seedling.*—Hybrid of *Prunus sargentii.*

Tree: Medium, upright, tall and hardy.
- *Height at maturity.*—16 meters. Maintains upright habit of parent.
- *Width.*—5½ meters. Broader than parent.

Trunk: Stocky and smooth.
- *Color.*—Strong brown 2.5 Y/R 4/7.

Branches: Stocky and smooth.
- *Branch angle.*–45°.
- *Color.*—Moderate yellowish brown, 10 YR 4/4.
- *Lenticels.*—Abundant — 8 per cm of twig length; color Strong brown 5Y/R 4/5.

Leaves:
- *Quantity.*—Abundant, large.
- *Length.*—13 to 16 cm.
- *Width.*—7 to 8 cm.
- *Shape.*—Oblong ovate, gradually acuminate.
- *Color.*—When expanding, Bronze color, 2.5 YR 5.9 Brownish Orange. In the summer — Moderate Olive Green 5 GY 4/3. in the fall — Strong Red 5R 3/7.
- *Margin.*—Serrate.
- *Petiole.*—Short, 2 to 3 cm long.
- *Glands.*—Average number 2, opposite, medium to small, Globose, color — Dark Red.
- *Stipules.*—Paired 1. to 1.5 cm long.

Flower buds:
- *Hardiness.*—Very hardy, to −10 degrees F.
- *Size.*—1 cm long; 0.5 cm wide.
- *Shape.*—Long and pointed.
- *Color.*—Dark Red, 5R 3/7.

Flowers:
- *Dates first bloom.*—April 8.
- *Full bloom.*—April 15.
- *Quantity.*—Dense, very abundant, 3 to 4 per cluster.
- *Size.*—Large — 4.5 cm. in diameter.

Petalage:
- *Number of petals.*—5.
- *Pedicels.*—2 cm long.
- *Shape of petals.*—Ovate with slightly notched tips (0.2 cm. deep).

*Size of petals.*—Length 2 cm; Width 1 cm.

*Color.*—Pure White.

Fruits: Not significant.

*Abundance.*—Sparse.

*Size.*—1.5 cm, globular.

*Color.*—Black.

Reproductive organs:

*Stamen.*—Anthers: Small — 1.2 cm long. Number — 10–12. Color — Vivid yellow 2.5Y 8/12. Arrangement — Regular around styles. Filaments: Threads — Short (1.2 cm long). Color — Brilliant yellow — 2.5Y 9/9.

*Pollen.*—Color — Vivid yellow 2.5Y 8/12.

*Styles.*—One central style per flower. Length — Short (1cm. long), thin.

*Stigmas.*—Number — One. Color — Vivid yellow 2.5Y 8/12.

*Ovaries.*—Number-one, enclosed in calyx.

I claim:

1. A new and distinct Prunus plant, substantially as herein shown and described, characterized particularly as to novelty by its very vigorous growth habit, by its very abundant, large white flowers, and by its cold hardiness in USDA hardiness zone 5-A.

* * * * *